United States Patent [19]
Akiyama et al.

[11] Patent Number: 5,948,773
[45] Date of Patent: Sep. 7, 1999

[54] FORMULATION COMPRISING ANTIBACTERIAL SUBSTANCE AND ANTIULCER SUBSTANCE

[75] Inventors: Yohko Akiyama, Ibaraki; Masafumi Nakao, Ikoma; Naoki Nagahara, Itami; Susumu Iwasa, Tsuzuki-gun, all of Japan

[73] Assignee: Takeda Chemical Industries, Ltd., Osaka, Japan

[21] Appl. No.: 08/863,293

[22] Filed: May 27, 1997

Related U.S. Application Data

[63] Continuation of application No. 08/303,674, Sep. 9, 1994, abandoned.

[30] Foreign Application Priority Data

Sep. 9, 1993 [JP] Japan ................................. 5-224707

[51] Int. Cl.⁶ .......................... A61K 31/43; A61K 34/44
[52] U.S. Cl. ............................................ 514/197; 514/338
[58] Field of Search ............................. 514/338; 54/197

[56] References Cited

U.S. PATENT DOCUMENTS

| | | | |
|---|---|---|---|
| 4,912,093 | 3/1990 | Michaeli | 514/53 |
| 5,045,321 | 9/1991 | Makino et al. | 514/394 |

FOREIGN PATENT DOCUMENTS

| | | |
|---|---|---|
| 2092694 | 3/1992 | Canada . |
| 0 205 282 | 12/1986 | European Pat. Off. . |
| 0 403 048 | 12/1990 | European Pat. Off. . |
| 0 282 132 | 9/1992 | European Pat. Off. . |
| 0 514 008 | 11/1992 | European Pat. Off. . |
| 0 533 281 | 3/1993 | European Pat. Off. . |
| 92/01457 | 2/1992 | WIPO . |
| 92/03135 | 3/1992 | WIPO . |
| 92/04898 | 4/1992 | WIPO . |
| 92/11849 | 7/1992 | WIPO . |
| 94/00112 | 1/1994 | WIPO . |

OTHER PUBLICATIONS

P. Unge et al., "Does Omeprazole Improve Antimicrobial Therapy Directed Towards Gastric *Campylobacter Pylori* in Patients with Antral Gastritis?", Scandinavian Journal of Gastroenterology, vol. 24, Supplement 167, 1989, pp. 49–54.

T. Shimoyama et al., Is it an Exaggeration to Say "No *Helicobacter pylori*, no ulcer?", Peptic Ulcer Review—Current Topics, Oct. 1992, with English translation.

*Primary Examiner*—Jerome D. Goldberg
*Attorney, Agent, or Firm*—Foley & Lardner

[57] ABSTRACT

The present invention includes a formulation which comprises an antibacterial substance and an antiulcer substance, wherein at least either of them is formulated into a gastrointestinal mucosa-adherent solid preparation. The formulation of the present invention shows long retention time in the gastrointestinal tract because of adhesion to the gastrointestinal tract mucosa, synergetically enhances the pharmaceutical effects of an antibacterial substance, specially antibiotic against *Helicobacter pylori* (HP) and an antiulcer substance, with very low doses of active ingredients, particularly the anti-HP antibiotic with low prevalence of side effects. The present agent is useful as an anti ulcer agent, showing potent anti-HP activity.

31 Claims, No Drawings

FORMULATION COMPRISING ANTIBACTERIAL SUBSTANCE AND ANTIULCER SUBSTANCE

This application is a continuation of application Ser. No. 08/303,674, filed Sep. 9, 1994, now abandoned.

FIELD OF THE INVENTION

The present invention relates to a formulation which comprises an antibacterial substance and an antiulcer substance, wherein at least either of them is formulated into a gastrointestinal mucosa-adherent solid preparation. The formulation of the present invention is used as an antiulcer agent and for other purposes.

BACKGROUND OF THE INVENTION

Since the isolation of *Helicobacter pylori* (hereinafter also referred to as HP) in 1983 [Lancet, 1, 1273 (1983)], its association with gastritis and digestive ulcer has drawn attention. This is because HP is found at high positivity rates in chronic gastritis or gastric ulcer [American Journal of Gastroenterology, 82, 2283 (1987)], despite the fact that it is normally not found in the mucosa of healthy humans [APMIS, 96, 84 (1988)].

On the other hand, the development of $H_2$ blockers and proton pump inhibitors (hereinafter also referred to as PPI) has resulted in markedly improved healing rates for gastric/duodenal ulcer. However, there are some contractile cases in which no improvement occurs despite the appropriate treatment using these drugs, posing major problems. According to a report of such cases of contractile gastric ulcer [Japanese Journal of Gastroenterology, 89, 571 (1992)], the HP positivity rate is extremely high, with a reduction in the amount of gastromucosal mucus attributable to the ammonia produced by HP. Also, there are some reports of sustained infection with HP which delays ulcer healing or which is involved in ulcer recurrence [Lancet, 335, 1233 (1990); New England Journal of Medicine, 328,308 (1993)]. Judging from these many clinical findings, HP elimination is believed to be useful in early healing of ulcer or prevention of its recurrence.

For the reasons described above, various anti-HP drugs have been administered to patients with gastric/duodenal ulcer. Although some PPIs possessing anti-HP activity have been developed, they remain unsatisfactory as to healing effect when used alone because their antibacterial action against HP is not always sufficient. Also, concomitant therapy has been performed with fair therapeutic results in which antiulcer agents such as $H_2$ blockers and PPI are used in combination with antibacterial substances [Medical Journal of Australia, 151, 431 (1988); George L L et al., Medical Journal of Australia, 13, 145 (1990); Peterson W L et al., New England Journal of Medicine, 324, 1043 (1991); New England Journal of Medicine, 328, 308 (1993)].

Antibacterial substances such as amoxicillin (hereinafter also referred to as AMOX), metronidazole (hereinafter also referred to as MZ), bismuth subacetate and tetracycline, have been used against HP singly or in combination; however, their administration often causes side effects such as diarrhea, nausea and retching because of the considerable doses (e.g., 750 mg of AMOX or 500 mg of MZ administered three times a day). Also, a pharmaceutical composition containing an anti-HP antibiotic (e.g., AMOX) and pantoprazol (WO 92/03135), and an administration comprising AMOX and omeprazole in combination (Scandinavian Journal of Gastroetherology, 24, 49 (1989) are reported, but their antiulcer action is unsatisfactory and their administration causes side effects as mentioned above.

Meantime, there have been developed gastrointestinal mucosa-adherent matrices to allow the preparation to adhere to the gastrointestinal mucosa to extend its retention in the gastrointestinal tract and hence improve the bioavailability of active ingredients. Although antiulcer agents, antigastritis agents etc. have been mentioned as active ingredients appropriate for use in the above-described preparation (EP-A-514008), none have been applied to formulation for concomitant therapy wherein at least one of them is prepared as a gastrointestinal mucosa-adherent solid preparation.

OBJECTS OF THE INVENTION

The main object of the present invention is to provide a formulation for treating a gastrointestinal ulcer which exhibits antiulcer effect with more potent anti-HP activity.

This object as well as other objects and advantages of the present invention will become apparent to those skilled in the art from the following description.

SUMMARY OF THE INVENTION

The present inventors investigated to obtain a safer therapeutic formulation for gastric/duodenal ulcer that exhibits antiulcer effect with more potent anti-HP activity. As a result, the present inventors found that a formulation comprising an anti-HP antibiotic and an antiulcer substance, wherein at least one is formulated into a gastrointestinal mucosa-adherent solid preparation, synergistically enhances the antibiotic's anti-HP activity, as well as the antiulcer the action of antiulcer substance due to the combined effect of both agents, thus providing a formulation of lower prevalence of side effects. The inventors made further investigations based on these findings, and developed the present invention.

According to the present invention, there is provided:

1) A formulation which comprises an antibacterial substance and an antiulcer substance, wherein at least one of them is formulated into a gastrointestinal muscosa-adherent solid preparation,
2) The formulation according to 1) above, wherein the antibacterial substance is an antibacterial substance against *Helicobacter pylori*,
3) The formulation according to 1) above, wherein the gastrointestinal mucosa-adherent solid preparation comprises a matrix containing a polyglycerin fatty acid ester,
4) The formulation according to 1) above, wherein the gastrointestinal mucosa-adherent solid preparation contains the antibacterial substance,
5) The formulation according to 1) above, wherein the antibacterial substance is a penicillin,
6) The formulation according to 1) above, wherein the antibacterial substance is a macrolide antibiotic,
7) The formulation according to 5) above, wherein the penicillin is amoxicillin,
8) The formulation according to 1) above, wherein the antiulcer substance is a proton pump inhibitor,
9) The formulation according to 8) above, wherein the proton pump inhibitor is a compound represented by the formula:

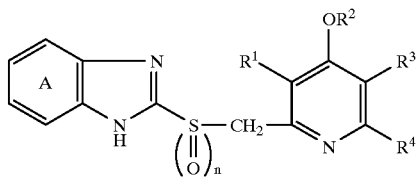

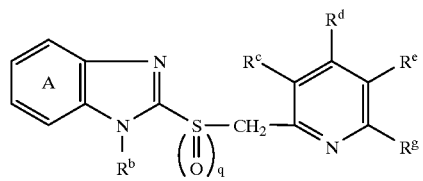

wherein ring A may optionally be substituted, $R^1$, $R^3$ and $R^4$ are, the same or different, hydrogen, or an alkyl or alkoxy group, $R^2$ is a hydrocarbon group which may optionally be substituted, and n is 0 or 1, or a salt thereof, 10) The formulation according to 3) above, wherein the gastrointestinal mucosa-adherent solid preparation comprises a viscogenic agent capable of developing viscosity on contact with water, 11) The formulation according to 10) above, wherein the viscogenic agent is dispersed in the gastrointestinal mucosa-adherent solid preparation, 12) The formulation according to 10) above, wherein the viscogenic agent coats the gastrointestinal mucosa-adherent solid preparation, 13) The formulation according to 10) above, wherein the viscogenic agent is an acrylic acid polymer or its salt, and 14) A set for the use in treating a gastrointestinal ulcer in mammals which comprises (1) an antibacterial substance and a pharmaceutically acceptable carrier thereof, and (2) an antiulcer substance and a pharmaceutically acceptable carrier thereof, wherein at least one of the substances is formulated into a gastrointestinal mucosa-adherent solid preparation.

Useful antibacterial substance for the invention include antibacterial substances against *Helicobacter pylori*, bismuth salt, imidazole compounds, quinolone compounds, and the like. Among others, antibacterial substances against *Helicobacter pylori* are preferred.

Useful antibacterial substance against *Helicobacter pylori* (HP) for the present invention include penicillin (e.g., amoxicillin, benzylpenicillin, piperacillin, mecillinam), cephem antibiotics (e.g., cefixime, cefaclor), macrolide antibiotics (e.g., erythromycin), tetracycline antibiotics (e.g., tetracycline, minocycline, streptomycin), aminoglycoside antibiotics (e.g, gentamycin, amikacin), imipenem, and the like. Among others, penicillin, macrolide antibiotics, tetracycline antibiotics and imipenem are preferred, and penicillin, macrolide antibiotics and imipenem are more preferred. Of these, amoxicillin and imipenem are particularly preferable because they exhibit strong antibacterial against HP at low concentrations, with greater preference given to amoxicillin.

Bismuth salts include bismuth subacetate, bismuth subcitrate, and so on. Imidazole compounds include metronidazole, miconazole, and so on. Quinolone compounds include ofloxacin, ciprofloxacin, and so on.

Useful antiulcer substances for the present invention include $H_2$ blockers, proton pump inhibitors, and the like. These substances may be used singly or in combination. Proton pump inhibitors are preferred. $H_2$ blockers include cimetidine, famotidine, ranitidine and derivatives or salts thereof. These $H_2$ blockers can be produced by, for example, the methods described in U.S. Pat. Nos. 3,950,333, 4,283,408 and 4,128,658, or modifications thereof.

Proton pump inhibitors include benzimidazole compounds. Preferable benzimidazole compounds include 2-[(pyridyl)-methylsulfinyl or -methylthio]benzimidazole derivatives and salts thereof. A compound (or salt thereof) represented by formula (I) below is more preferred.

wherein ring A may optionally be substituted; $R^b$ is a hydrogen atom, an alkyl group, an acyl group, a carboalkoxy group, a carbamoyl group, an alkylcarbamoyl group, a dialkylcarbamoyl group or an alkylsulfonyl group; $R^c$, $R^e$, and $R^g$ are, the same of different, a hydrogen atom, an alkyl group, an alkoxy group or an alkoxyalkoxy group; $R^d$ is a hydrogen atom, an alkyl group or a group represented by —$OR^f$ in which $R^f$ represents a hydrocarbon group which may optionally be substituted; q is 0 or 1.

Benzimidazole compounds above are described in U.S. Pat. No. 4,045,563, U.S. Pat. No. 4,255,431, U.S. Pat. No. 4,359,465, U.S. Pat. No. 4,472,409, U.S. Pat. No. 4,508,905, JP-A-59181277, U.S. Pat. No. 4,628,098, U.S. Pat. No. 4,738,975, U.S. Pat. No. 5,045,321, U.S. Pat. No. 4,786,505, U.S. Pat. No. 4,853,230, U.S. Pat. No. 5,045,552, EP-A-295603, U.S. Pat. No. 5,312,824, EP-A-166287, EP-A-519365, and other publications.

With respect to formula (I) above, the substituent that may optionally be present on ring A includes halogen atoms, alkyl groups which may be substituted for, cycloalkyl groups which may be substituted for, alkenyl groups which may be substituted for, alkoxy groups which may be substituted for, cyano groups, carboxy groups, carboalkoxy groups, carboalkoxyalkyl groups, carbamoyl groups, carbamoylalkyl groups, hydroxy groups, hydroxyalkyl groups, acyl groups, carbamoyloxy groups, nitro groups, acyloxy groups, aryl groups, aryloxy groups, alkylthio groups and alkylsulfinyl groups, and the like.

The above substituents are hereinafter described.

Halogen atoms include fluorine, chlorine, bromine and iodine. Fluorine and chlorine are preferred, with greater preference given to fluorine.

The alkyl group in the alkyl group which may be substituted is exemplified by straight-chain or branched alkyl groups having 1 to 10 carbon atoms (e.g., methyl, ethyl, n-propyl, isopropyl, n-butyl, isobutyl, sec-butyl, tert-butyl, n-pentyl, isopentyl, neopentyl, hexyl, heptyl, octyl, nonyl, decyl). Straight-chain or branched alkyl groups having 1 to 6 carbon atoms are preferred, with greater preference given to straight-chain or branched alkyl groups having 1 to 3 carbon atoms. Substituents on the substituted alkyl group include halogens, nitro, cyano groups, hydroxy groups, carboxy groups, amidino groups, guanidino groups, carbamoyl groups, amino groups which may have 1 to 2 alkyl groups, acyl groups or other substituents, and the like.

The cycloalkyl group in the cycloalkyl group which may be substituted is exemplified by cycloalkyl groups having 3 to 7 carbon atoms, such as cyclopropyl, cyclobutyl, cyclopentyl, cyclohexyl and cycloheptyl etc. The cycloalkyl group may be substituted by, for example, halogens, nitro, cyano groups, hydroxy groups, carboxy groups, amidino groups, guanidino groups, carbamoyl groups, amino groups which may have 1 to 2 alkyl groups, acyl groups or other substituents, and the like.

The alkenyl group in the alkenyl group which may be substituted is exemplified by straight-chain or branched alkenyl groups having 2 to 16 carbon atoms. Such alkenyl groups include allyl, vinyl, crotyl, 2-penten-1-yl, 3-penten-1-yl, 2-hexen-1-yl, 3-hexen-1-yl, 2-methyl-2-propen-1-yl and 3-methyl-2-buten-1-yl. Straight-chain or branched alkenyl groups having 2 to 6 carbon atoms are preferred, with greater preference given to straight-chain or branched alkenyl groups having 2 to 4 carbon atoms. The alkenyl group may be substituted by, for example, halogens, nitro, cyano groups, amidino groups, guanidino groups amino groups which may have 1 to 2 alkyl groups, acyl groups or other substituents, and the like. The alkenyl group mentioned above includes isomers (E- and Z-configurations) with respect to double bond.

The alkoxy group in the alkoxy group which may be substituted is exemplified by alkoxy groups having 1 to 10 carbon atoms. Such alkoxy groups include methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy and cyclohexyloxy. Alkoxy groups having 1 to 6 carbon atoms are preferred, with greater preference given to alkoxy groups having 1 to 3 carbon atoms. The alkoxy group may be substituted by, for example, halogens, nitro, amidino groups, guanidino groups amino groups which may have 1 to 2 alkyl groups, acyl groups or other substituents, and the like.

The halogen as a substituent on the above-described alkyl, cycloalkyl, alkenyl or alkoxy group is exemplified by chlorine, bromine, fluorine and iodine.

The alkyl group in the alkylamino group as a substituent on the above-described alkyl, cycloalkyl, alkenyl or alkoxy group is preferably exemplified by straight-chain or branched alkyl groups having 1 to 6 carbon atoms. Such alkyl groups include methyl, ethyl, n-propyl, isopropyl, n-butyl, isobutyl, tert-butyl, sec-butyl, n-pentyl, isopentyl, n-hexyl and isohexyl. Among others, straight-chain or branched alkyl groups having 1 to 4 carbon atoms are preferred.

The acyl group in the acylamino group as a substituent on the above-described alkyl, cycloalkyl, alkenyl or alkoxy group is exemplified by acyl groups derived from organic carboxylic acids, with preference given to alkanoyl groups having 1 to 6 carbon atoms. Such alkanoyl groups include formyl, acetyl, propionyl, butyryl, isobutyryl, valeryl, isovaleryl, pivaloyl and hexanoyl, with greater preference given to alkanoyl groups having 1 to 4 carbon atoms.

The number of substituents on the above-described alkyl, cycloalkyl, alkenyl or alkoxy group is 1 to 6, preferably 1 to 3.

The substituted alkyl groups include trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxyethyl, 2,2-diethoxyethyl and 2-diethylphosphorylethyl, among others. Difluoromethyl, trifluoromethyl and hydroxymethyl are preferred, with greater preference given to trifluoromethyl.

The substituted cycloalkyl groups include 2-aminocyclopropan-1-yl, 4-hydroxycyclopentan-1-yl and 2,2-difluorocyclopentan-1-yl, among others. The substituted alkenyl groups include 2,2-diclorovinyl, 3-hydroxy-2-propen-1-yl and 2-methoxyvinyl, among others.

The substituted alkoxy groups include difluoromethoxy, trifluoromethoxy, 2,2,2-trifluoroethoxy, 2-methoxyethoxy, 4-chlorobenzyloxy and 2-(3,4-dimethoxyphenyl)ethoxy, among others. Difluoromethoxy is preferred.

The alkoxy group in the carboalkoxy group is exemplified by alkoxy groups having 1 to 7 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy).

The alkoxy group in the carboalkoxyalkyl group is exemplified by alkoxy groups having 1 to 4 carbon atoms (e.g., methoxy, ethoxy, n-propoxy, isopropoxy, n-butoxy, isobutoxy, sec-butoxy, tert-butoxy). The alkyl group in the carboxyalkoxyalkyl group is exemplified by alkyl groups having 1 to 4 carbon atoms (e.g., methyl, ethyl, n-propyl, isopropyl, n-butyl, isobutyl, sec-butyl, tert-butyl). Such carboalkoxyalkyl groups include carbomethoxymethyl, 2-carbomethoxyethyl, 2-carbomethoxypropyl, carboethoxymethyl, 2-carboethoxyethyl, 1-carbomethoxypropyl, carbopropoxymethyl and carbobutoxymethyl.

The alkyl group in the carbamoylalkyl group is exemplified by alkyl groups having 1 to 4 carbon atoms (e.g., methyl, ethyl, n-propyl, isopropyl, n-butyl, isobutyl, sec-butyl, tert-butyl).

The alkyl group in the hydroxyalkyl group is exemplified by alkyl groups having 1 to 7 carbon atoms (e.g., methyl, ethyl, n-propyl, isopropyl, n-butyl, isobutyl, sec-butyl, tert-butyl, n-pentyl, isopentyl, neopentyl, hexyl, heptyl).

The acyl group as such or the acyl group in the acyloxy group is exemplified by alkanoyl groups having 1 to 4 carbon atoms such as formyl, acetyl, propionyl, butyryl and isobutyryl.

The aryl group as such or the aryl group in the aryloxy group is exemplified by aryl groups having 6 to 12 carbon atoms (e.g., phenyl, naphthyl).

The alkyl in the alkylthio group or alkylsulfinyl group is exemplified by alkyl groups having 1 to 6 carbon atoms (e.g., methyl, ethyl, n-propyl, isopropyl, n-butyl, isobutyl, sec-butyl, tert-butyl, n-pentyl, isopentyl, neopentyl, hexyl).

The number of substituents on substituted ring A is preferably 1 to 4, more preferably 1 to 2. Such substituents on the benzene ring may be present at 4- and 5-positions, with preference given to 5-position.

Ring A is preferably A ring which may optionally be substituted by i) a halogen atom ii), an alkyl group which may be substituted, iii) a cycloalkyl group which may be substituted, iv) an alkenyl group which may be substituted, or v) an alkoxy group which may be substituted.

The alkyl group for $R^b$ is exemplified by alkyl groups having 1 to 5 carbon atoms (e.g., methyl, ethyl, n-propyl, isopropyl, n-butyl, isobutyl, sec-butyl, tert-butyl, n-pentyl, isopentyl, neopentyl). The acyl group for $R^b$ is exemplified by acyl groups having 1 to 4 carbon atoms, such as alkanoyl groups having 1 to 4 carbon atoms. The alkoxy in the carboalkoxy group is exemplified by alkoxy groups having 1 to 4 carbon atoms (e.g., formyl, acetyl, propionyl, butyryl, isobutyryl). The alkyl in the alkylcarbamoyl group and dialkylcarbamoyl group is exemplified by alkyl groups having 1 to 4 carbon atoms (e.g., methyl, ethyl, n-propyl, isopropyl, n-butyl, isobutyl, sec-butyl, tert-butyl). The alkyl in the alkylsulfonyl group is exemplified by the above-mentioned alkyl groups having 1 to 4 carbon atoms. $R^b$ is preferably hydrogen.

The alkyl group for $R^c$, $R^e$ or $R^g$ is exemplified by straight-chain or branched alkyl groups having 1 to 10 carbon atoms (e.g., methyl, ethyl, n-propyl, isopropyl, n-butyl, isobutyl, sec-butyl, tert-butyl, n-pentyl, isopentyl, neopentyl, hexyl, heptyl, octyl, nonyl, decyl). Straight-chain or branched alkyl groups having 1 to 6 carbon atoms are preferred, with greater preference given to straight-chain or branched alkyl groups having 1 to 3 carbon atoms.

The alkoxy group for $R^c$, $R^e$ or $R^g$ is exemplified by alkoxy groups having 1 to 10 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy). Alkoxy groups having 1 to 6 carbon atoms are preferred, with greater preference given to alkoxy groups having 1 to 3 carbon atoms.

The alkoxy in the alkoxyalkoxy group for $R^c$, $R^e$ or $R^g$ is exemplified by alkoxy groups having 1 to 4 carbon atoms (e.g., methoxy, ethoxy, n-propoxy, isopropoxy, n-butoxy, isobutoxy, sec-butoxy, tert-butoxy).

$R^c$ is preferably a hydrogen atom, an alkyl group or an alkoxy group. $R^e$ is preferably a hydrogen atom, an alkyl group or an alkoxy group. $R^g$ is preferably a hydrogen atom.

The alkyl group for $R^d$ is exemplified by alkyl groups having 1 to 4 carbon atoms (e.g., methyl, ethyl, n-propyl, isopropyl, n-butyl, isobutyl, sec-butyl, tert-butyl).

The hydrocarbon group in the hydrocarbon group which may optionally be substituted, for $R^f$, is exemplified by hydrocarbon groups having 1 to 13 carbon atoms, such as straight-chain or branched alkyl groups having 1 to 6 carbon atoms (e.g., methyl, ethyl, propyl, isopropyl, butyl, isobutyl, sec-butyl, pentyl, isopentyl, hexyl), alkenyl groups having 2 to 6 carbon atoms (e.g., vinyl, allyl, 2-butenyl, methylallyl, 3-butenyl, 2-pentenyl, 4-pentenyl, 5-hexenyl), alkenyl groups having 2 to 6 carbon atoms (e.g., ethynyl, propargyl, 2-butyl-1-yl, 3-butyl-2-yl, 1-pentyn-3-yl, 3-pentyn-1-yl, 4-pentyn-2-yl, 3-hexyn-1-yl), cycloalkyl groups having 3 to 6 carbon atoms (e.g., cyclopropyl, cyclobutyl, cyclopentyl, cyclohexyl), cycloalkenyl groups having 3 to 6 carbon atoms (e.g., cyclobutenyl, cyclopentenyl, cyclohexenyl, cyclohexadienyl), aralkyl groups having 7 to 13 carbon atoms (e.g., benzyl, 1-phenetyl, 2-phenetyl) and aryl groups having 6 to 10 carbon atoms (e.g., phenyl, naphthyl). Straight-chain or branched alkyl groups having 1 to 6 carbon atoms (e.g., methyl, ethyl, propyl, isopropyl, butyl, isobutyl, sec-butyl, pentyl, isopentyl, hexyl) are preferred, with greater preference given to straight-chain or branched alkyl groups having 1 to 4 carbon atoms.

The substituent group in the substituted hydrocarbon group is exemplified by $C_{6-10}$ aryl groups (e.g., phenyl, naphthyl), amino, $C_{1-6}$ alkylamino groups (e.g., methylamino, ethylamino, isopropylamino), di-$C_{1-6}$ alkylamino groups (e.g., dimethylamino, diethylamino), N-aralkyl-N-cycloalkylamino groups (e.g., N-benzyl-N-cyclohexylamino), N-aralkyl-N-alkylamino groups (e.g., N-(1-naphthylmethyl)-N-ethylamino), azide, nitro, halogens (e.g., fluorine, chlorine, bromine, iodine), hydroxyl, $C_{1-4}$ alkoxy groups (e.g., methoxy, ethoxy, propoxy, butoxy), $C_{6-10}$ aryloxy groups (e.g., phenoxy, naphthyloxy), $C_{1-6}$ alkylthio groups (e.g., methylthio, ethylthio, propylthio), $C_{6-10}$ arylthio groups (e.g., phenylthio, naphthylthio), cyano, carbamoyl groups, carboxyl groups, $C_{1-4}$ alkoxycarbonyl groups (e.g., methoxycarbonyl, ethoxycarbonyl), $C_{7-11}$ aryloxycarbonyl groups (e.g., phenoxycarbonyl, 1-naphthyloxycarbonyl, 2-naphthyloxycarbonyl), carboxy-$C_{1-4}$ alkoxy groups (e.g., carboxymethoxy, 2-carboxyethoxy), $C_{1-6}$ alkanoyl groups (e.g., formyl, acetyl, propionyl, isopropionyl, butyryl, pentanoyl, hexanoyl), $C_{7-11}$ alloyl groups (e.g., benzoyl, 1-naphthoyl, 2-naphthoyl), $C_{6-10}$ arylsulfonyl groups (e.g., benzenesulfonyl, 1-naphthylsulfonyl, 2-naphthylsulfonyl), $C_{1-6}$ alkylsulfinyl groups (e.g., methylsulfinyl, ethylsulfinyl), $C_{6-10}$ arylsulfinyl groups (e.g., benzenesulfinyl, 1-naphthylsulfinyl, 2-naphthylsulfinyl), $C_{1-6}$ alkylsulfonyl groups (e.g., methylsulfonyl, ethylsulfonyl), 5- or 6-membered heterocyclic groups (e.g., 2-furyl, 2-thienyl, 4-thiazolyl, 4-imidazolyl, 4-pyridyl, 1,3, 4-thiadiazol-2-yl, 1-methyl-5-tetrazolyl) containing 1 to 4 hetero atoms (e.g., nitrogen, oxygen, sulfur), 5- or 6-membered heterocyclic carbonyl groups (e.g., 2-furoyl, 2-thienoyl, nicotinoyl, isonicotinoyl) containing 1 to 4 hetero atoms (e.g., nitrogen, oxygen, sulfur), 5- or 6-membered heterocyclic thio groups (e.g., 4-pyridylthio, 2-pyrimidylthio, 1,3,4-thiadiazol-2-ylthio, 1-methyl-5-tetrazolylthio) containing 1 to 4 hetero atoms (e.g., nitrogen, oxygen, sulfur). The heterocyclic thio group may condense with the benzene ring to form a bicyclic condensed thio group (e.g., 2-benzothiazolylthio, 8-quinolylthio). Halogens (e.g., fluorine, chlorine, bromine, iodine), hydroxyl and $C_{1-4}$ alkoxy groups (e.g., methoxy, ethoxy, propoxy, butoxy) are preferred.

The number of substituents is normally 1 to 5, preferably 1 to 3.

$R^d$ is preferably an alkoxy group which may be substituted, or an alkoxyalkoxy group which may be substituted. The alkoxy in the alkoxy group which may be substituted is exemplified by alkoxy groups having 1 to 8 carbon atoms (e.g., methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy). The alkoxy in the alkoxyalkoxy group which may be substituted is exemplified by alkoxy groups having 1 to 4 carbon atoms (e.g., methoxy, ethoxy, n-propoxy, isopropoxy, n-butoxy, isobutoxy, sec-butoxy, tert-butoxy). $R^d$ is more preferably an alkoxy group having 1 to 8, preferably 1 to 4 carbon atoms, which may be halogenated, or an alkoxyalkoxy group which may be halogenated. Preferred alkoxy groups which may be halogenated include 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy, 2,2,3,3, 4,4,5,5-octafluoropentoxy and methoxy. Preferred alkoxyalkoxy groups which may be halogenated include 3-methoxypropoxy.

q is preferably 0.

More specifically, the benzimidazole compound for the present invention is exemplified by a compound represented by formula (II):

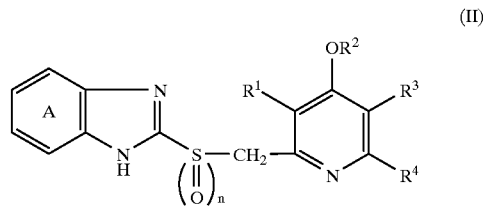

(II)

wherein ring A may optionally be substituted; $R^1$, $R^3$ and $R^4$ are, the same or different, hydrogen, or an alkyl or alkoxy group; $R^2$ is a hydrocarbon group which may optionally be substituted; n is 0 or 1.

With respect to formula (II) above, ring A is exemplified by the same rings as those mentioned for ring A of formula (I) above.

The alkyl group for $R^1$, $R^3$ or $R^4$ is exemplified by straight-chain or branched alkyl groups having 1 to 10 carbon atoms. Such alkyl groups include methyl, ethyl, n-propyl, isopropyl, n-butyl, isobutyl, sec-butyl, tert-butyl, n-pentyl, isopentyl, neopentyl, hexyl, heptyl, octyl, nonyl and decyl. Straight-chain or branched alkyl groups having 1 to 6 carbon atoms are preferred, with greater preference given to straight-chain or branched alkyl groups having 1 to 3 carbon atoms.

The alkoxy group for $R^1$, $R^3$ or $R^4$ is exemplified by alkoxy groups having 1 to 10 carbon atoms. Such alkoxy groups include methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy and cyclohexyloxy. Alkoxy groups having 1 to 6 carbon atoms are preferred, with greater preference given to alkoxy groups having 1 to 3 carbon atoms.

The hydrocarbon group which may optionally be substituted, for $R^2$, is exemplified by the same hydrocarbon groups as those mentioned for $R^f$ above.

$R^1$ is preferably $C_{1-6}$ alkyl or $C_{1-6}$ alkoxy, more preferably $C_{1-3}$ alkyl.

$R^3$ is preferably hydrogen or $C_{1-6}$ alky, more preferably hydrogen.

$R^2$ is preferably $C_{1-4}$ alkoxy which may optionally be substituted by i) halogen, ii) hydroxyl or iii) $C_{1-4}$ alkoxy, more preferably, $C_{1-3}$ alkyl which may optionally be substituted by i) halogen or ii) $C_{1-4}$ alkoxy.

$R^4$ is preferably hydrogen.

Example benzimidazole compounds for the present invention include 2-[2-[3-methyl-4-(2,2,3,3-tetrafluoropropoxy)pyridyl]methylthio]benzimidazole (hereinafter referred to as Compound A), 2-[2-[3-methyl-4-(2,2,2-trifluoroethoxy)pyridyl]methylsulfinyl] benzimidazole (lansoprazole), 2-[(2-pyridyl)methylsulfinyl] benzimidazole (timoprazole), 2-[2-(3,5-dimethyl-4-methoxypyridyl)methylsulfinyl]-5-methoxy-1H-benzimidazole (omeprazole), sodium salt of 2-[2-[4-(3-methoxypropoxy)-3-methylpyridyl]methylsulfinyl]-1H-benzimidazole and 2-[2-(3,4-dimethoxy)pyridyl] methylsulfinyl]-5-difluoromethoxy-1H-benzimidazole (pantoprazole).

A benzimidazole compound (or salt thereof) for the present invention is produced by, for example, the above-described known methods described in Japanese or European Patent Publications and U.S. Patents, or modifications thereof.

The salt of a benzimidazole compound is preferably used as a physiologically acceptable salt. Physiologically acceptable salts include salts with inorganic bases, salts with organic bases and salts with basic amino acids. Useful inorganic bases include alkali metals (e.g., sodium, potassium) and alkaline earth metals (e.g., calcium, magnesium). Useful organic bases include trimethylamine, triethylamine, pyridine, picoline, N,N-dibenzylethylenediamine, ethanolamine, diethanolamine, trishydroxymethylaminomethane and dicyclohexylamine. Useful basic amino acids include arginine and lysine.

These salts are produced by known methods such as those described in EP-A-295603 and U.S. Pat. No. 4,738,974, or modifications thereof.

The formulation of the present invention is used as (1) a combination of an antiulcer substance and a gastrointestinal mucosa-adherent solid preparation containing an antibacterial substance, (2) a combination of an antibacterial substance and a gastrointestinal mucosa-adherent solid preparation containing an antiulcer substance, (3) a gastrointestinal mucosa-adherent solid preparation containing both an antibacterial substance and an antiulcer substance, or (4) a combination of a gastrointestinal mucosa-adherent solid preparation containing an antibacterial substance and a gastrointestinal mucosa-adherent solid preparation containing an antiulcer substance. The combination of an antiulcer substance and a gastrointestinal mucosa-adherent solid preparation containing an antibacterial substance is preferred.

The gastrointestinal mucosa-adherent solid preparation containing an antibacterial substance and/or an antiulcer substance may be any gastrointestinal mucosa-adherent solid preparation, as long as it adheres to a particular site in the gastrointestinal tract, its retention time in the gastrointestinal tract is long and/or it promotes absorption of active ingredients at the absorption site. Useful such preparations include gastrointestinal mucosa-adherent solid preparation which comprises matrixes containing a polyglycerin fatty acid ester. Preferred is a gastrointestinal mucosa-adherent solid preparation which comprises matrixes containing a polyglycerin fatty acid and a substance which develops viscosity on contact with water (hereinafter also referred to as viscogenic agent). Furthermore, gastrointestinal mucosa-adherent matrixes comprising a lipid and a viscogenic agent may be also useful in the present invention. Preferably, a gastrointestinal mucosa-adherent matrix comprising a polyglycerin fatty acid ester and a viscogenic agent is used. With respect to the gastrointestinal mucosa-adherent matrix, it is preferable that a viscogenic agent be dispersed in a matrix containing a polyglycerin fatty acid ester or a lipid, or a matrix containing a polyglycerin fatty acid ester or a lipid is coated with a viscogenic agent. The melting point of the gastrointestinal mucosa-adherent matrix is about 30–120° C., preferably about 40–120° C.

The polyglycerin fatty acid ester may be of any type, whether mono-, di- or poly-ester, as long as it is an ester of polyglycerol and fatty acid. Polyglycerin fatty acid esters are stable over an extended period, with almost no deactivation of active ingredients, in the presence of active ingredients, because they show no crystalline polymorphism and show almost no interaction with active ingredients.

A polyglycerol is defined as "a polyhydric alcohol having n (cyclic) to (n+2) (linear or branched) hydroxyl groups and (n−1) (linear or branched) to n (cyclic) ether linkages in each molecule" [Polyglycerol Ester, edited by Sakamoto Yakuhin Kogyo Co., Ltd., published May 2, 1986, p. 12]. The polyglycerol may be linear or branched. It is exemplified by a compound represented by formula (III) below:

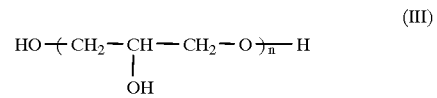

(III)

wherein n representing a degree of polymerization is an integer of at least 2. In the above formula (III), n is normally integer of 2 to 50, preferably 2 to 20, and more preferably 2 to 10. Such polyglycerins include diglycerol, triglycerol, tetraglycerol, pentaglycerol, hexaglycerol, heptaglycerol, octaglycerol, nonaglycerol, decaglycerol, pentadecaglycerol, eicosaglycerol and triacontaglycerol. Of these polyglycerols, tetraglycerol, hexaglycerol and decaglycerol, for example, are commonly used.

The fatty acids of the polyglycerin fatty acid include saturated or unsaturated fatty acids having 8 to 40 carbon atoms, preferably 12 to 22 carbon atoms. Such fatty acids include palmitic acid, stearic acid, oleic acid, linolic acid, linolenic acid, myristic acid, lauric acid, ricinoleic acid, caprylic acid, capric acid and behenic acid. Of these fatty acids, stearic acid, oleic acid, lauric acid, linolic acid and behenic acid are preferred.

Example of polyglycerin fatty acid esters include behenic acid hexa(tetra)glyceride, caprylic acid mono(deca) glyceride, caprylic acid di(tri)glyceride, capric acid di(tri) glyceride, lauric acid mono(tetra)glyceride, lauric acid mono(hexa)glyceride, lauric acid mono(deca)glyceride, oleic acid mono(tetra)glyceride, oleic acid mono(hexa) glyceride, oleic acid mono(deca)glyceride, oleic acid di(tri) glyceride, oleic acid di(tetra)glyceride, oleic acid sesqui (deca)glyceride, oleic acid penta(tetra)glyceride, oleic acid penta(hexa)glyceride, oleic acid deca(deca)glyceride, linolic acid mono(hepta)glyceride, linolic acid di(tri)glyceride, linolic acid di(tetra)glyceride, linolic acid di(hexa)glyceride, stearic acid mono(d)glyceride, stearic acid mono(tetra) glyceride, stearic acid mono(hexa)glyceride, stearic acid mono(deca)glyceride, stearic acid tri(tetra)glyceride, stearic acid tri(hexa)glyceride, stearic acid sesqui(hexa)glyceride, stearic acid penta(tetra)glyceride, stearic acid penta(hexa) glyceride, stearic acid deca(deca)glyceride, palmitic acid mono(tetra)glyceride, palmitic acid mono(hexa)glyceride, palmitic acid mono(deca)glyceride, palmitic acid tri(tetra) glyceride, palmitic acid tri(hexa)glyceride, palmitic acid sesqui(hexa)glyceride, palmitic acid penta(tetra)glyceride, palmitic acid penta(hexa)glyceride and palmitic acid deca (deca)glyceride. Preferable polyglycerin fatty acid esters include behenic acid hexa(tetra)glyceride [e.g., Poem J-46B (trade name), produced by Riken Vitamin K.K., HB-310 (trade name), produced by Sakamoto Yakuhin Kogyo K.K.], stearic acid penta(tetra)glyceride [e.g., PS-310 (trade name), produced by Sakamoto Yakuhin Kogyo K.K.], stearic acid mono(tetra)glyceride[e.g., MS-310 (trade name), produced by Sakamoto Yakuhin Kogyo K.K.], stearic acid penta(hexa) glyceride [e.g., PS-500 (trade name), produced by Sakamoto Yakuhin Kogyo K.K.], stearic acid sesqui(hexa)glyceride [e.g., SS-500 (trade name), produced by Sakamoto Yakuhin Kogyo K.K.], stearic acid mono(deca)glyceride and mixtures thereof.

The above polyglycerin fatty acid esters can be used singly or in combination.

The molecular weight of the polyglycerin fatty acid ester is normally about 200 to about 5,000, preferably about 300 to about 2,000, and more preferably about 500 to about 2,000. The HLB (hydrophile-lipophile balance) of the polyglycerin fatty acid ester is normally 1 to 22, preferably 1 to 15, and more preferably 2 to 9. Two or more polyglycerin fatty acid esters of different HLB values may be mixed as appropriate to obtain the desired HLB level. Adjusting the HLB of a polyglycerin fatty acid ester makes it possible to control the release and dissolution of active ingredients.

Polyglycerin fatty acid esters can be selected as appropriate according to the forms of active ingredients, viscogenic agent and matrix; those which are solid at normal temperature (about 15° C.) are used. The melting point of the polyglycerin fatty acid ester is normally about 15–80° C., preferably about 30–75° C., and more preferably 45–75° C.

When two or more polyglycerin fatty acid esters are used in mixture, they may be used in combination with liquid polyglycerin fatty acid esters, as long as the gastrointestinal mucosa-adherent matrix is solid at normal temperature.

As for lipids, those whose melting point is about 40 to about 120° C., preferably about 40 to about 90° C. are used.

Lipids include saturated fatty acids having 14 to 22 carbon atoms (e.g., myristic acid, palmitic acid, stearic acid, behenic acid) or salts thereof (e.g., sodium salt, potassium salt), higher alcohols having 16 to 22 carbon atoms (e.g., cetyl alcohol, stearyl alcohol), fatty acid glycerol esters which are mono-, di- or tri-glycerides with the above fatty acids (e.g., 1-monostearin, 1-monopalmitin), oils and fats (e.g., castor oil, cottonseed oil, soybean oil, rapeseed oil, beef tallow, etc., and hardened oils/fats thereof), waxes (e.g., beeswax, carnauba wax, spermaceti), hydrocarbons (e.g., paraffin, microcrystalline wax) and phospholipids (e.g., hydrogenated lecithin). Preferred among these lipids are oils and fats, waxes, saturated fatty acids having 14 to 20 carbon atoms, higher alcohols having 16 to 20 carbon atoms, hydrocarbons and the like. Of these lipids, hardened cottonseed oil, hardened castor oil, hardened soybean oil, carnauba wax, stearic acid, stearyl alcohol and microcrystalline wax are preferred.

The viscogenic agent capable of developing viscosity on contact with water (viscogenic agent) is not subject to limitation, as long as it becomes viscous and adherent to the gastrointestinal tract mucosa upon exposure to water, and as long as it is pharmaceutically acceptable. Of such viscogenic agents, those which swell and become highly viscous upon exposure to water are preferred. Viscogenic agents include polymers and natural viscous substances. Preferably, such polymers have a viscosity of about 3 to 50,000 cps, preferably about 10 to 30,000 cps, and more preferably about 15 to 30,000 cps as of 2% aqueous solution. In the case of polymers which become viscous upon neutralization, however, the viscosity at 20° C. is normally about 100 to 500,000 cps, preferably about 100 to 200,000 cps, more preferably about 1,500 to 100,000 cps as of 0.2% neutral solution.

Such polymer includes acid polymers, preferably polymers having carboxyl or sulfo groups or salts thereof. Among others, polymers having carboxyl groups or a salts thereof are more preferred.

Polymers having the carboxyl groups or salts thereof include acrylic acid polymers (including copolymers) comprising acrylic acid monomer units, and salts thereof. Such salts include salts of monovalent metals, such as sodium salt and potassium salt, and salts of divalent metals, such as magnesium salt and calcium salt. Acrylic acid polymers or salts thereof include polymers containing 58–63% by weight of carboxyl groups and having a molecular weight of 200,000 to 6,000,000, preferably 1,000,000 to 5,000,000. Preferable acrylic acid polymers or salts thereof include acrylic acid homopolymers and salts thereof. Such polymers are described as carboxyvinyl polymers in the Non-official Drugs Standards of Japan (October, 1986). Examples of such polymers include carbomers [Carbopol, trade name, The B.F. Goodrich Company)] 940, 934, 934P, 940, 941, 1342 (NF XVII) etc., Hiviswako 103, 104, 105 (Wako Pure Chemical Industries), NOVEON AA1 [trade name of The B.F. Goodrich Company] and calcium polycarbophil (USP XXII).

Natural viscous substances include mucin, agar, gelatin, pectin, carrageenan, sodium alginate, locust bean gum, xanthane gum, tragacanth gum, gum arabic, chitosan, pullulan and waxy starch, sucralfate, cellulose and its derivatives (e.g. cellulose sulfate etc.).

The viscogenic agents for the present invention is preferably an acrylic acid polymer and its salt.

These viscogenic agents may be used singly or in combination.

The amount of viscogenic agent used is normally about 0.005 to about 99% by weight, preferably about 0.5 to about 45% by weight, and more preferably about 1 to about 30% by weight, in the gastrointestinal mucosa-adherent matrix. For example, when a viscogenic agent is dispersed in the matrix containing a polyglycerin fatty acid ester or a lipid, the viscogenic agent normally accounts for about 0.005 to about 95% by weight, preferably about 0.5 to about 30% by weight, and more preferably about 5 to about 25% by weight of the total weight. When the matrix is covered with a viscogenic agent, the viscogenic agent normally accounts for about 0.005 to about 95% by weight, preferably about 0.5 to about 30% by weight, and more preferably about 5 to about 25% by weight, of the total weight.

When the gastrointestinal mucosa-adherent matrix used is a gastrointestinal mucosa-adherent matrix comprising a polyglycerin fatty acid ester and a viscogenic agent contained therein, a gastrointestinal mucosa-adherent matrix comprising a lipid and a viscogenic agent contained therein or the like, the amounts of polyglycerin fatty acid ester and lipid used are about 0.001 to 10,000 times, preferably about 0.001 to 50 times, the amount of active ingredients in the solid preparation, based on weight.

The above-described matrix containing a polyglycerol fatty acid ester may incorporate a lipid. The lipid is a pharmaceutically acceptable water-insoluble substance which serves to control the dissolution rate of active ingredients, exemplified by the above-mentioned lipids.

When a lipid and a polyglycerol fatty acid ester are used in combination, the amount of lipid used is chosen over the range within which its adhesion to the gastrointestinal tract mucosa is not interfered with, e.g., about 0.01 to 100 times, preferably about 1 to 20 times, the amount of active ingredients, based on weight.

The above-described gastrointestinal mucosa-adherent solid preparation may be used in combination with an appropriate amount of organic acid to promote the absorption of active ingredients. Organic acids include tartaric acid, citric acid, succinic acid and ascorbic acid.

The above-described solid preparation may also incorporate additives commonly used to produce solid pharmaceuticals (e.g., fine subtilaes, granules). Such additives include excipients such as lactose, corn starch, talc, crystalline cellulose (e.g., Avicel), powder sugar, magnesium stearate, mannitol, light silicic anhydride, magnesium carbonate, calcium carbonate and L-cysteine, binders such as starch, sucrose, gelatin, gum arabic powder, methyl cellulose, carboxymethyl cellulose, carboxymethyl cellulose sodium, hydroxypropyl cellulose, hydroxypropylmethyl cellulose, polyvinylpyrrolidone, pullulan and dextrin, disintegrating agents such as carboxymethyl cellulose calcium, low-substitutional hydroxypropyl cellulose and cross carmellose sodium, surfactants, e.g., anionic surfactants such as sodium alkylsulfate and nonionic surfactants such as polyoxyethylene sorbitan fatty acid ester, polyoxyethylene fatty acid ester and polyoxyethylene castor oil derivative, antacids or mucosa protectors such as magnesium hydroxide, magnesium oxide, aluminum hydroxide, aluminum sulfate, magnesium metasilicate aluminate, magnesium silicate aluminate and sucralfate, coloring agents, tasting agents, adsorbents, antiseptics, wetting agents, antistatic agents and disintegration extenders. The amount of these additives added is chosen as appropriate over the range within which adhesion to the mucosa is not lost.

With respect to the above-described gastrointestinal mucosa-adherent solid preparation comprising a viscogenic agent dispersed in a matrix containing a polyglycerol fatty acid ester or a lipid, the polyglycerol fatty acid ester or lipid, viscogenic agent and active ingredients are dispersed in the solid preparation. This dispersion is achieved by known methods.

The above-described gastrointestinal mucosa-adherent solid preparation is produced by known methods. For example, a polyglycerol fatty acid ester or lipid is molten by heating above the melting point thereof, and a viscogenic agent and active ingredients are dispersed simultaneously or separately, followed by cooling. Heating temperature is normally about 40 to about 150° C., preferably about 50 to about 110° C., and more preferably about 50 to about 90° C.

The above method can be achieved using a common granulator; it is preferable to prepare the gastrointestinal mucosa-adherent solid preparation as a spherical solid preparation (e.g., fine subtilaes) by, for example, spray chilling. Spray chilling can be achieved by adding drop by drop a mixture of a viscogenic agent and active ingredients dispersed in the molten polyglycerol fatty acid ester or lipid at a constant flow rate on a high-speed rotary disk rotating at 10 to 6,000 rpm, preferably 900 to 6,000 rpm, and more preferably 1,000 to 3,000 rpm. Useful rotary disks include smooth disks, such as aluminum disks, of 5 to 100 cm, preferably 10 to 20 cm in diameter. The dropping speed for the molten mixture can be chosen according to the desired particle size, and is normally about 2 to 200 g/min, preferably about 5 to 100 g/min. The grains thus obtained make it possible to efficiently form a uniform coating film in the later coating process because they are almost truly spherical.

In addition to the above method, the desired gastrointestinal mucosa-adherent solid preparation can be prepared by dispersing and granulating a polyglycerol fatty acid ester or lipid, viscogenic agent and active ingredients by kneading etc. In this case, common solvents (e.g., methanol, acetonitrile, chloroform) are used.

The gastrointestinal mucosa-adherent solid preparation can also be produced by melting granulation. Melting granulation can be achieved by the method in which a polyglycerol fatty acid ester or a lipid is thermally molten near the melting point thereof, e.g., about 5° C. below the melting point, and then granulated, subjecting the resultant melt to granulation, for example by spray chilling, to prepare fine granules, and fluidizing the resultant granules together with the viscogenic agent and active ingredients in a current of air under mild heating to provide a medicated mucosa-adherent matrix. In this case, since thermal action on the active ingredients is suppressed, the desired solid preparation can easily be obtained while suppressing the inactivation of the active ingredients, even when the active ingredients are peptides, proteins or the like.

With respect to the above-described gastrointestinal mucosa-adherent solid preparation wherein a matrix containing a polyglycerol fatty acid ester or a lipid is coated with a viscogenic agent, the solid preparation itself may be coated by a viscogenic agent, preferably by a coating agent containing at least a viscogenic agent. In addition to the above viscogenic agent, the coating agent may contain at least one component selected from the group consisting of the above-described polyglycerol fatty acid esters, the above-described lipids and water-insoluble polymers. In this case, when using a viscogenic agent is poorly compatible or incompatible with the above-described components of the solid preparation, the solid preparation can be coated by a film containing the viscogenic agent dispersed therein. The coating agent may contain additives.

Water-insoluble polymers include hydroxypropylmethyl cellulose phthalate (JP XI), hydroxypropylmethyl cellulose acetate succinate (produced by Shin-Etsu Chemical Co., Ltd.), carboxymethylethyl cellulose (CMEC, produced by Freund Industrial Co., Ltd., Non-official Drugs Standards of Japan, 1986), cellulose acetate trimellitate (produced by Eastman), cellulose acetate phthalate (JP XI), ethyl cellulose (FMC, produced by Asahi Chemical Industry Co., Ltd.), aminoalkyl methacrylate copolymer (Eudragit E100, trade name, produced by Rohm Pharma Company), aminoalkyl methacrylate copolymer (Eudragit RS, RN100L, RSPML, RN100, RSPM, trade names, produced by Rohm Pharma Company), methacrylic acid copolymer L (Eudragit L100, trade name, produced by Rohm Pharma Company), methacrylic acid copolymer L-D (Eudragit L-30-D-55, trade name, produced by Rohm Pharma Company), methacrylic acid copolymer S (Eudragit S-100, trade name, produced by Rohm Pharma Company), polyvinyl acetate phthalate (produced by COLORCON), and Eudragit NE3O-D (trade name, produced by Rohm Pharma Company). These water-insoluble polymers may be used singly or in combination.

The amount of the viscogenic agent used in the coating agent is normally about 0.005 to about 100% by weight, preferably about 0.05 to about 95% by weight, more preferably about 0.05 to about 30% by weight, and still more preferably about 1 to about 10% by weight of the total solid content of the coating agent.

When at least one polyglycerol fatty acid ester, lipid or water-insoluble polymer and a viscogenic agent are used in combination as coating agents, the viscogenic agent accounts for about 0.005 to about 95% by weight, preferably about 0.5 to about 30% by weight, and more preferably about 5 to about 25% by weight of the total solid content of the coating agent.

In the coating agent, two or more components selected from the group consisting of polyglycerol fatty acid esters, lipids and water-insoluble polymers can be used in combination. In this case, relative to 1 part by weight of the total of the polyglycerol fatty acid ester and/or lipid, the other components account for about 0.0001 to 1,000 parts by weight, preferably about 0.01 to 100 parts by weight, and more preferably about 0.01 to 10 parts by weight.

The amount of coating agent coated can be chosen as appropriate according to kind of solid preparation, adhesion to the target mucous and other factors. The coating amount to the solid preparation is normally 0.1 to about 30% by weight, preferably about 0.5 to about 10% by weight for tablets, 0.1 to about 50% by weight, preferably about 1 to about 20% by weight for pills and granules, and 0.1 to about 100% by weight, preferably about 1 to about 50% by weight for fine subtilaes.

In coating, the above-mentioned commonly used additives may be added to the coating agent as necessary, and may be coated separately from the above-mentioned additives. The amount of additives used is normally 0.1 to about 70% by weight, preferably about 1 to about 50% by weight, and more preferably 20 to about 50% by weight of the total solid content of the coating agent.

Known coating methods can be used, including pan coating, fluidization coating and tumbling coating. When the coating agent is a solution or dispersion in water or an organic solvent, spray coating is also applicable. The amount of such water or organic solvent is about 25 to about 99% by weight. Any kind of organic solvent can be used, including alcohols such as methanol, ethanol and isopropyl alcohol, ketones such as acetone, and halogenated hydrocarbons such as chloroform, dichloromethane and trichloroethane.

When the coating agent incorporates a polyglycerol fatty acid ester and/or a lipid, it may be prepared as a coated preparation by mixing the polyglycerol fatty acid ester and/or the lipid and, where necessary, other additives, in a thermally molten state, emulsifying the mixture in water, spraying the emulsion over the surface of a solid preparation and drying. It may also be prepared as a coated preparation by melting and extending a coating agent over a solid preparation, preheated by hot blow, in an apparatus such as a coating pan.

The solid preparation is normally coated at about 25 to about 60° C., preferably about 25 to about 40° C.

Coating time can be chosen as appropriate in view of coating method, coating agent properties, amount of use, solid preparation properties and other factors.

The gastrointestinal mucosa-adherent solid preparation may be coated with a commonly used gastrically soluble or water-soluble film etc. as necessary, as long as the mucosa adhesion of the above-described viscogenic agent is retained in the gastrointestinal tract.

Example dosage forms of gastrointestinal mucosa-adherent solid preparations include fine subtilaes, granules, pills, tablets prepared by tableting fine subtilaes or granules, and capsules prepared by packing fine subtilaes or granules in capsules. Fine subtilaes and granules are preferred. Particle size distribution of fine subtilaes is normally such that 10 to 500 $\mu$m particles account for not less than 75% by weight, 500 $\mu$m or greater particles account for not more than 5% by weight, and 10 $\mu$m or smaller particles account for not more than 10% by weight. Preferably, particle size distribution of fine subtilaes is such that 105 to 500 $\mu$m particles account for not less than 75% by weight, 500 $\mu$m or greater particles account for not more than 5% by weight, and 74 $\mu$m or smaller particles account for not more than 10% by weight. Particle size distribution of granules is normally such that 500–1,410 $\mu$m particles account for not less than 90% by weight and 177 $\mu$m or smaller particles account for not more than 5% by weight.

The formulation of the present invention serves well, as long as at least one of the two components antibacterial substance and antiulcer substance is formulated into a gastrointestinal mucosa-adherent solid preparation. For example, 1) the antibacterial substance alone is formulated into a gastrointestinal mucosa-adherent solid preparation, 2) the antiulcer substance alone is formulated into a gastrointestinal mucosa-adherent solid preparation, 3) the antibacterial substance and the antiulcer substance are both prepared as gastrointestinal mucosa-adherent solid preparations at the same time or separately. Preferably, the antibacterial substance alone is formulated into a gastrointestinal mucosa-adherent solid preparation.

When one active ingredient is formulated into a gastrointestinal mucosa-adherent solid preparation, the other is used in a pharmaceutical composition along with a pharmacologically acceptable carrier or excipient, prepared by, e.g., granulating active ingredients by a known method (e.g., tablets, granules, fine subtilaes, capsules), or previously preparing active ingredients as aqueous solution, by preparing active ingredients as a solid mixture by lyophilization, an aqueous solution of active ingredients is solidified by lyophilization, by dispersing active ingredients in oil, and dispersing active ingredients in syrup. The formulation of the present invention may be prepared in a set in which each component constitutes a separate preparation.

The formulation of the present invention is normally used orally or non-orally in a pharmaceutical composition comprising these active ingredients and a pharmacologically acceptable carrier or excipient.

For the formulation of the present invention, the above active ingredients are mixed to a single preparation using pharmaceutically acceptable diluents, excipients and other additives as desired by a known method of pharmaceutical production. Each active ingredient may be prepared as a separate preparation using pharmaceutically acceptable diluents, excipients and other additives as desired. Alternatively, separate preparations may be combined to a set. For example, the formulation of the present invention can be used in (1) a set comprising an antiulcer substance and a gastrointestinal mucosa-adherent solid preparation containing an antibacterial substance, (2) a set comprising an antibacterial substance and a gastrointestinal mucosa-adherent solid preparation containing an antiulcer substance, (3) a set comprising a gastrointestinal mucosa-adherent solid preparation containing both an antibacterial substance and an antiulcer substance, or (4) a set comprising a gastrointestinal mucosa-adherent solid preparation containing an antibacterial substance and a gastrointestinal mucosa-adherent solid preparation containing an antiulcer substance.

When active ingredients are prepared as separate preparations, they may be administered to the same individual at the same time or at time intervals via the same route or different routes.

The contents of the antibacterial substance and antiulcer substance in the formulation of the present invention may be chosen as appropriate on a case-by-case basis; for example, the concentration of the antibacterial substance is normally about 0.1–95% by weight, preferably about 1–95% by weight, and more preferably about 10–90% by weight. The antiulcer substance concentration is normally about 0.1 to 95% by weight, preferably about 1 to 95% by weight, and more preferably about 10 to 90% by weight.

The ratio of the antibacterial substance used to the antiulcer substance is normally about 0.001 to 100 times (by weight), preferably about 0.005 to 15 times (by weight), of the antiulcer substance content, although it varies depending on combinations.

Example compositions for oral administration include tablets, pills, granules, powders, capsules, syrups, emulsions and suspensions. These compositions are produced by known methods, using lactose, starch, sucrose, magnesium stearate and other substances as carriers or excipients.

Compositions for non-oral administration can be prepared as suppositories or external preparations.

Suppositories include rectal suppositories and vaginal suppositories. External preparations include ointments (including creams), vaginal preparations, transnasal preparations and percutaneous preparations.

For a suppository, a composition of the present invention may be prepared as an oily or aqueous solid, semi-solid or liquid suppository by a known method.

The formulation of the present invention is useful in the treatment of mammals (e.g., cats, dogs, bovines, horses, goats, monkeys, humans) carrying Helicobacter pylori, exhibiting marked effect in removing Helicobacter pylori carried by these animals. Target diseases include gastrointestinal ulcer, such as gastritis and digestive ulcer, with particular effect obtained in the treatment of digestive ulcer.

With low toxicity, the formulation of the present invention can be administered orally or non-orally to mammals including humans. It may be used in mixture with pharmacologically and pharmaceutically acceptable additives (e.g., diluents, excipients, binders, disintegrating agents, colorants, stabilizers), or as prepared using them, in the same manner as above, as desired. Although the dose of the formulation of the present invention varies depending on dosage form, administration method, kind of active ingredients used and other factors. The antibacterial substance requirements can be reduced to less than the usual clinical dose, for example to about one-half to about one-tenth. It is preferable that the antibacterial substance and antiulcer substance be administered at about 0.2 to 10 mg/kg and about 0.05 to 40 mg/kg daily for a human adult. More preferably, the daily dose is about 0.3 to 6 mg/kg as of the antibacterial substance and about 0.1 to 15 mg/kg as of the antiulcer substance.

With respect to the formulation of the present invention, an antibacterial substance and an antiulcer substance, separately prepared, may be administered to the same subject at the same time, or they may be administered to the same subject at a time interval in that order or reverse order. Components may have different administration frequencies.

The formulation of the present invention shows long retention time in the gastrointestinal tract because of its adhesion to the gastrointestinal tract mucosa, synergetically enhances the pharmaceutical effects of an antibacterial substance and an antiulcer substance, with very low, doses of active ingredients, particularly the anti-HP antibiotic, e.g. about one-half to about one-tenth of the usual clinical dose, with low prevalence of side effects. The present agent is useful as an antiulcer agent, showing potent anti-HP activity.

The following reference examples and working examples are intended to illustrate of the present invention in further detail.

REFERENCE EXAMPLE 1

In vitro determination of activity against *Helicobacter pylori*

Method: 2 ml of a solution of the test antibiotic, in 2-fold serial dilution, was placed in a petri dish. To this dish, 18 ml of 7 w/w % bullsera agar supplemented with horse blood, previously dissolved at about 50° C., was added, followed by uniform stirring and solidification at room temperature, to yield an agar plate for actual measurement. Next, after inoculation of 5 $\mu$l of a $10^6$ CFU/ml bacterial suspension, the plate was incubated at 37° C. for 4 days under slightly aerobic conditions in a gas pack jar containing CampyPak™ (BBL Company, USA) and water-soaked defatted cotton. The antibiotics used here were benzylpenicillin, amoxicillin, piperacillin, mecillinam, imipenem, erythromycin, tetracycline and streptomycin. Bacterial strains used were (1) *Helicobacter pylori* NCTC 11637, (2) *Helicobacter pylori* NCTC 11916 and (3) *Helicobacter pylori* CPY 433.

Antibacterial activity was determined by minimum antibiotic concentration for macroscopic bacterial growth.

Results: As determined by the above method, benzylpenicillin, amoxicillin, piperacillin, mecillinam, imipenem, erythromycin, tetracycline and streptomycin all failed to allow bacterial growth of any of the above three at concentrations under 1.0 $\mu$/ml, demonstrating strong antibacterial activity.

REFERENCE EXAMPLE 2

Production of gastrointestinal mucosa-adherent solid preparation containing Compound A 12 g of behenic acid hexa(tetra)glyceride (HB-310, trade name, produced by Sakamoto Yakuhin K.K.) was thermally molten at 85° C., and 4 g of Compound A and 4 g of a poly (acrylic acid) (Hiviswako 104, Wako Pure Chemical Industries) were added, followed by stirring at 80° C. for 15 minutes, to yield a dispersion. The resulting molten mixture was added drop by drop to an aluminum disk of 15 cm in diameter rotating at 1,500 rpm at 10 g/min to yield spherical fine subtilaes which pass through a 30-mesh sieve but not through an 80-mesh sieve (hereinafter referred to as 30/80 mesh).

REFERENCE EXAMPLE 3

Production of gastrointestinal mucosa-adherent solid preparation containing amoxicillin (AMOX)

75 g of behenic acid hexa(tetra)glyceride (HB-310, trade name, produced by Sakamoto Yakuhin K.K.) was thermally molten at 74° C., and 10 g of AMOX and 15 g of a poly (acrylic acid) (Hiviswako 104, Wako Pure Chemical Industries) were added, followed by stirring at 74° C. for 15 minutes, to yield a dispersion. The resulting molten mixture was added drop by drop to an aluminum disk of 15 cm in diameter rotating at 2,400 rpm at 10 g/min to yield 30/80 mesh spherical fine subtilaes.

For oral administration in humans or non-human animals, 100 mg of the above fine subtilaes was packed in No. 4 capsules to yield a capsular preparation.

REFERENCE EXAMPLE 4

Production of gastrointestinal mucosa-adherent solid preparation containing Compound A 27.5 g of behenic acid hexa(tetra)glyceride (HB-310, trade name, produced by Sakamoto Yakuhin K.K.) was thermally molten at 85° C., and 8 g of Compound A, 7.5 g of a poly (acrylic acid) (Hiviswako 104, Wako Pure Chemical Industries) and 10 g of tartaric acid were added, followed by stirring at 80° C. for 15 minutes, to yield a dispersion. The resulting molten mixture was added drop by drop to an aluminum disk of 15 cm in diameter rotating at 2,400 rpm at 10 g/min to yield 30/80 mesh spherical fine subtilaes.

EXAMPLE 1

Production of gastrointestinal mucosa-adherent solid preparation containing both Compound A and AMOX To 65 g of behenic acid hexa(tetra)glyceride (HB-310, trade name, produced by Sakamoto Yakuhin K.K.), thermally molten at 74° C., 15 g of Compound A, 5 g of AMOX and 15 g of a poly (acrylic acid) (Hiviswako 104, Wako Pure Chemical Industries) were added, followed by stirring at 74° C. for 15 minutes, to yield a dispersion. The resulting molten mixture was added drop by drop to an aluminum disk of 15 cm in diameter rotating at 2,400 rpm at 10 g/min to yield 30/80 mesh spherical fine subtilaes containing both Compound A and AMOX.

EXAMPLE 2

Production of formulation comprising of a gastrointestinal mucosa-adherent solid preparation containing AMOX and a gastrointestinal mucosa-adherent solid preparation containing Compound A 50 mg of a gastrointestinal mucosa-adherent solid preparation containing Compound A as obtained in Reference Example 2 and 100 mg of a gastrointestinal mucosa-adherent solid preparation containing AMOX as obtained in Reference Example 3 were packed in No. 4 capsules to yield a capsular preparation.

EXAMPLE 3

Production of formulation comprising Compound A and a gastrointestinal mucosa-adherent solid preparation containing AMOX Using a fluidized bed granulator (FD-35, Powrex), granules containing Compound A were obtained as follows; Specifically, an aqueous dispersion containing 10 mg of Compound A was sprayed over a powder consisting of 72 mg of lactose and 18 mg of corn starch, and an aqueous solution containing 4 mg of hydroxypropyl cellulose was sprayed, followed by granulation, drying and size uniformization, to yield granules containing Compound A.

100 mg of the granules containing Compound A thus obtained and 100 mg of a gastrointestinal mucosa-adherent solid preparation containing AMOX as obtained in Reference Example 3 were packed in No. 3 capsules to yield capsules.

EXAMPLE 4

Synergistic effect of Compound A and a gastrointestinal mucosa-adherent solid preparation containing AMOX Crj:ICR mice (4 animals per group), fasted for 30 hours, were infected with *Helicobacter pylori* CPY 433 by oral gastric addition ($10^{7.3}$ cells/mouse). Thirteen days later, ① a gastrointestinal mucosa-adherent solid preparation containing AMOX as obtained in Reference Example 3 (referred to as ① solitary drug in Table 1), and ② a 0.5% methyl cellulose suspension containing Compound A and a gastrointestinal mucosa-adherent solid preparation containing AMOX as obtained in Reference Example 3 (referred to as ② combination agent in Table 1), were orally administered at 50 mg/kg AMOX and 30 mg/kg Compound A, respectively. At 6, 16, 24 and 48 hours after administration, stomachs were excised, gastric wall distribution products and gastric washings were each inoculated to selection medium for HP, followed by 4 days of incubation under slightly aerobic conditions; viable cells were counted to obtain bacterial removal rates (negative mice/all mice). The results are given in Table 1.

Here, the number of mice showing negative response to HP in the stomach is shown as the bacterial removal rate.

TABLE 1

| | Bacterial Removal Rate* | | | |
|---|---|---|---|---|
| Hours after Drug Administration | Gastric Wall Disruption Product | | Gastric Washings | |
| | ① Solitary Agent | ② Combination Agent | ① Solitary Agent | ② Combination Agent |
| 0 (control) | 0/4 | 0/4 | 0/4 | 0/4 |
| 6 | 0/4 | 0/4 | 1/4 | 0/4 |
| 16 | 2/4 | 4/4 | 3/4 | 4/4 |
| 24 | 3/4 | 4/4 | 4/4 | 4/4 |
| 48 | 1/4 | 3/4 | 1/4 | 3/4 |

*Bacterial removal rate: Number of mice showing negative response to *Helicobacter pylori*/number of all mice When Compound A and the gastrointestinal mucosa-adherent solid preparation containing AMOX was administered, all mice became negative 16 hours after administration, while when the gastrointestinal mucosa-adherent solid preparation containing AMOX alone was administered, half mice showed positive response to HP in the gastric wall.

EXAMPLE 5

Synergistic effect of Compound A and a gastrointestinal mucosa-adherent solid preparation containing AMOX Methyl cellulose was suspended in distilled water to 0.5% by weight. To 1 ml of this suspension, 0.045 mg of AMOX and 4.5 mg of Compound A were added, to yield a mixed suspension in methyl cellulose.

In the same manner as in Example 4, Crj:ICR mice (5 to 6 animals per group), fasted for 30 hours, were infected with *Helicobacter pylori* CPY 433. Starting at 13 days after infection, ① the above mixed suspension of AMOX and Compound A in methyl cellulose (referred to as ① suspension in Table 2), and ② a 0.5% suspension of Compound A and a gastrointestinal mucosa-adherent solid preparation containing AMOX as obtained in Reference Example 3 in methyl cellulose (referred to as ② AMOX and Compound A combination preparation in Table 2) were orally administered for 7 consecutive days at 0 mg/kg or 0.3 mg/kg for AMOX and 30 mg/kg for Compound A. At 20 hours after administration, stomachs were excised, gastric wall disruption products and gastric washings were tested to obtain bacterial removal rates in the same manner as in Example 4. The results are given in Table 2.

TABLE 2

| | Bacterial Removal Rate* | | | |
|---|---|---|---|---|
| | ① Suspension | | ② AMOX and Compound A Combination Preparation | |
| AMOX Concentration (mg/kg) | Gastric Wall | Gastric Washings | Gastric Wall | Gastric Washings |
| 0 | 0/5 | 0/5 | 0/6 | 0/6 |
| 0.3 | 2/5 | 2/5 | 5/6 | 5/6 |

*Bacterial removal rate: Number of mice showing negative response to Helicobacter pylori/number of all mice In comparison with administration of a mixed suspension of AMOX and Compound A in methyl cellulose, administration of a preparation comprising Compound A and a gastrointestinal mucosa-adherent solid preparation containing AMOX resulted in potent anti-HP activity in mice.

EXAMPLE 6

Production of a formulation comprising lansoprazole and a gastrointestinal mucosa-adherent solid preparation containing AMOX 1) Granules containing lansoprazole was prepared as follows.

| Ingredients | mg |
|---|---|
| Lansoprazole | 30 |
| Magnesium Carbonate USP | 22.4 |
| Sugar Spheres NF | 110.0 |
| Sucrose NF | 59.8 |
| Starch NF | 36.4 |
| Low-Substituted Hydroxypropyl Cellulose NF (L-HPC-31) | 40.0 |
| Hydroxypropyl Cellulose NF (HPC-L) | 1.4 |
| Methacrylic Acid Copolymer LD (Eudragit L30D-55) (Röhm Pharma Co.) | 44.6 |
| Polyethylene Glycol NF (PEG-6000) | 4.4 |
| Titanium Dioxide USP | 4.4 |
| Polysorbate 80 NF (Rheodol TW-0120) | 2.0 |
| Talc USP | 14.0 |
| Colloidal Silicon Dioxide NF (Aerosil) | 0.6 |
| Purified water * USP | q.s. |
| Total | 370.0 |

*: Removed during the manufacturing process
USP: The United States Pharmacopeia
NF: The National Formulary Sugar spheres was coated with a mixture of lansoprazole, magnesium carbonate, sucrose, starch and L-HPC-31 by means of spraying aqueous HPC-L solution in a centrifugal fluid-bed granulator (CF-1000S, Freund Co.), and the resultant wet granules were dried in a vacuum oven at about 40° C. for about 18 hours, and then sieved. The obtained granules were coated with aqueous enteric Eudragit suspension containing PEG-6000, talc, titanium dioxide and Rheodol TW-0120 in a fluid-bed coater (F10-Coater FLO-60, Freund Co.), and sieved, and then dried in a vacuum oven at about 42° C. for about 18 hours. The obtained granules were mixed with talc and Aerosil.

2) 370 mg of granules containing lansoprazole as obtained in 1) above and 100 mg of gastrointestinal mucosa-adherent solid preparation containing AMOX as obtained in Reference Example 3 were packed in No.0 capsules to yield a capsule preparation.

What we claim is:

1. A formulation which comprises about 10 to 90% by weight based on the weight of the formulation of an antibacterial substance comprising amoxicillin and about 10 to 90% by weight based on the weight of the formulation of an antiulcer substance comprising a benzimidazole compound, wherein the antibacterial substance is formulated into a gastrointestinal mucosa-adherent solid preparation, and wherein the ratio of the antibacterial substance to antiulcer substance is about 0.005 to 15 by weight of the antiulcer content.

2. The formulation according to claim 1, wherein the gastrointestinal mucosa-adherent solid preparation further comprises a matrix containing a polyglycerin fatty acid ester.

3. The formulation according to claim 2, wherein the gastrointestinal mucosa-adherent solid preparation comprises a viscogenic agent capable of developing viscosity on contact with water.

4. The formulation according to claim 3, wherein the viscogenic agent is dispersed in the gastrointestinal mucosa-adherent solid preparation.

5. The formulation according to claim 3, wherein the viscogenic agent coats the gastrointestinal mucosa-adherent solid preparation.

6. The formulation according to claim 3, wherein the viscogenic agent is an acrylic acid polymer or its salt.

7. The formulation according to claim 1, wherein the benzimidazole compound is a compound represented by the formula:

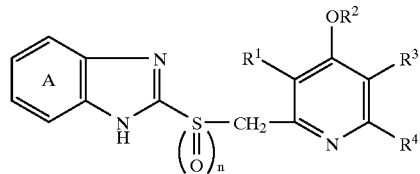

wherein ring A may optionally be substituted, $R^1$, $R^3$ and $R^4$ are, the same or different, hydrogen, or an alkyl or alkoxy group, $R^2$ is a hydrocarbon group which may optionally be substituted, and n is 0 or 1, or a salt thereof.

8. The formulation according to claim 1, wherein the benzimidazole compound is 2-[3-methyl-4-(2,2,3,3-tetraflouropropoxy)pyridyl]methylthio]benzimidazole.

9. A method for treating a gastrointestinal ulcer in a mammal which comprises administering to the mammal a therapeutically effective amount of the formulation according to claim 1.

10. The method according to claim 9, wherein the antibacterial substance and the antiulcer substance are administered simultaneously.

11. The method according to claim 9, wherein the antibacterial substance and the antiulcer substance are administered sequentially.

12. A method for removing Helicobacter pylori in a mammal which comprises administering to the a mammal a therapeutically effective amount of the formulation according to claim 1.

13. A formulation according to claim 1, wherein both the antibacterial substance and the antiulcer substance are formulated into the same gastrointestinal mucosa-adherent solid preparation.

14. A formulation according to claim 1, wherein the antibacterial substance and the antiulcer substance are formulated into separate gastrointestinal mucosa-adherent solid preparations.

15. A formulation according to claim 1, wherein only the antibacterial substance is formulated into the gastrointestinal mucosa-adherent solid preparation.

16. A formulation according to claim 1, wherein the antiulcer substance comprises 2-[2[3-methyl-4-(2,2,2trifluoroethoxy)pyridyl]methylsulfinyl]benzimidazole.

17. A formulation according to claim 16, wherein the gastrointestinal mucosa-adherent solid preparation comprises a matrix containing a polyglycerin fatty acid ester.

18. A formulation according to claim 16, wherein the gastrointestinal mucosa-adherent solid preparation comprises a viscogenic agent capable of developing viscosity on contact with water.

19. A formulation according to claim 18, wherein the viscogenic agent is dispersed in the gastrointestinal mucosa-adherent solid preparation.

20. A formulation according to claim 18, wherein the viscogenic agent coats the gastrointestinal mucosa-adherent solid preparation.

21. A formulation according to claim 18, wherein the viscogenic agent is an acrylic acid polymer or its salt.

22. A method for treating a gastrointestinal ulcer in a mammal which comprises administering to the mammal a therapeutically effective amount of the formulation according to claim 16.

23. A method according to claim 22, wherein the antibacterial substance and the antiulcer substance are administered simultaneously.

24. A method according to claim 22, wherein the antibacterial substance and the antiulcer substance are administered sequentially.

25. A method for removing *Helicobacter pylori* in a mammal which comprises administering to the mammal a therapeutically effective amount of the formulation according to claim 16.

26. A formulation according to claim 16, wherein both the antibacterial substance and the antiulcer substance are formulated into the same gastrointestinal mucosa-adherent solid preparation.

27. A formulation according to claim 16, wherein the antibacterial substance and the antiulcer substance are formulated into separate gastrointestinal mucosa-adherent solid preparations.

28. A formulation according to claim 16, wherein only the antibacterial substance is formulated into the gastrointestinal mucosa-adherent solid preparation.

29. A formulation for the use in treating a gastrointestinal ulcer in mammals which comprises (1) about 1–95% by weight based on the weight of the formulation of an antibacterial substance comprising amoxicillin and a pharmaceutically acceptable carrier thereof, and (2) about 1–95% by weight based on the weight of the set of an antiulcer substance comprising a benzimidazole compound and a pharmaceutically acceptable carrier thereof, wherein the antibacterial substance is formulated into a gastrointestinal mucosa-adherent solid preparation, and wherein the ratio of the antibacterial substance to antiulcer substance is about 0.005 to 15 by weight.

30. A formulation according to claim 29, wherein the antiulcer substance comprises 2-[2[3-methyl-4-(2,2,2-trifluoroethoxy) pyridyl]methylsulfinyl]benzimidazole.

31. A formulation for the use in treating a gastrointestinal ulcer in mammals which comprises (1) about 10–90% by weight based on the weight of the formulation of an antibacterial substance comprising amoxicillin and a pharmaceutically acceptable carrier thereof, and (2) about 10–90% by weight based on the weight of the set of an antiulcer substance comprising a benzimidazole compound and a pharmaceutically acceptable carrier thereof, wherein the antibacterial substance is formulated into a gastrointestinal mucosa-adherent solid preparation, and wherein the ratio of the antibacterial substance to antiulcer substance is about 0.005 to 15 by weight.

* * * * *

UNITED STATES PATENT AND TRADEMARK OFFICE
CERTIFICATE OF CORRECTION

PATENT NO.    : 5,948,773
DATED         : September 7, 1999
INVENTOR(S)   : Yohko Akiyama et al.

It is certified that error appears in the above-identified patent and that said Letters Patent is hereby corrected as shown below:

Column 22,
Line 44, delete "2-[3-methyl-4-(2,2,3,3-tetraflouropropoxy)pyridyl]methylthio]benzimidazole" and insert therefor -- 2-[2-[3-methyl-4-(2,2,3,3-tetrafluoropropoxy)pyridyl]methylthio]benzimidazole --

Column 23,
Line 5, delete "2-[2[3-methyl-4-(2,2,2trifluoroethoxy)pyridyl]methylsulfinyl]benzimidazole" and insert therefor -- 2-[2-[3-methyl-4-(2,2,2-trifluoroethoxy)pyridyl]methylsulfinyl]benzimidazole --.

Signed and Sealed this

Ninth Day of July, 2002

Attest:

JAMES E. ROGAN
Attesting Officer                Director of the United States Patent and Trademark Office